(12) United States Patent
Rosenbloom (10) Patent No.: US 7,507,425 B2
(45) Date of Patent: Mar. 24, 2009

(54) METHOD FOR THE TREATMENT OF CACHEXIA

(75) Inventor: Richard Allen Rosenbloom, North Wales, PA (US)

(73) Assignee: The Quigley Corporation, Doylestown, PA (US)

( * ) Notice: Subject to any disclaimer, the term of this patent is extended or adjusted under 35 U.S.C. 154(b) by 0 days.

(21) Appl. No.: 11/535,187

(22) Filed: Sep. 26, 2006

(65) Prior Publication Data

US 2007/0071838 A1    Mar. 29, 2007
US 2008/0241287 A9    Oct. 2, 2008

Related U.S. Application Data

(60) Provisional application No. 60/721,889, filed on Sep. 29, 2005, provisional application No. 60/720,969, filed on Sep. 27, 2005.

(51) Int. Cl.
*A01N 65/00* (2006.01)
*A61K 36/31* (2006.01)
*A61K 36/906* (2006.01)

(52) U.S. Cl. .................. 424/725; 424/729; 424/755; 424/756

(58) Field of Classification Search .................. None
See application file for complete search history.

(56) References Cited

U.S. PATENT DOCUMENTS

| | | | |
|---|---|---|---|
| 74,205 | A | 2/1868 | Dietz |
| 5,385,734 | A | 1/1995 | Friedman |
| 6,436,450 | B1 * | 8/2002 | Omary et al. ............... 424/755 |
| 6,465,517 | B1 * | 10/2002 | Van Der Zee ............... 514/562 |
| 6,541,045 | B1 * | 4/2003 | Charters et al. ............. 424/737 |
| 6,592,896 | B2 | 7/2003 | Rosenbloom |
| 6,596,313 | B2 | 7/2003 | Rosenbloom |
| 6,827,945 | B2 | 12/2004 | Rosenbloom |
| 2003/0185912 | A1 * | 10/2003 | Rosenbloom ............... 424/729 |
| 2003/0185918 | A1 * | 10/2003 | Rosenbloom ............... 424/755 |
| 2004/0253256 | A1 * | 12/2004 | Cheung ................. 424/195.16 |
| 2005/0123631 | A1 * | 6/2005 | Newmark et al. ........... 424/729 |
| 2005/0147697 | A1 | 7/2005 | Rosenbloom |
| 2005/0192342 | A1 | 9/2005 | Thompson |
| 2006/0147989 | A1 | 7/2006 | Rosenbloom |

OTHER PUBLICATIONS

"TNF and Interferon-Gamma Target Myosin Heavy Chain in Cancer Cachexia," Cancer Biology & Therapy, 2004, vol. 3, No. 11.

Fujiki, H. et al., "New TNF-Alpha Releasing Inhibitors as Cancer Preventive Agents from Traditional Herbal Medicine and Combination Cancer Prevention Study with EGCG and Sulindac or Tamoxifen," Mutation Research, 2003, pp. 119-125, Elsevier Science B.V.

Schuster, Michael and Yeh, Shing-Shing, "Progress Notes: Nutrition in Cancer Care," Nutrition, 2001, vol. 17, pp. 438-442.

Eylar, Edward H. et al., "HIV Infection and Aging: Enhanced Interferon- and Tumor Necrosis Factor-Alpha Production by the CD8+ CD28- T Subset," BMC Immunology, 2001, vol. 2, No. 10.

"Hope for Patients with Chronic Kidney Disease, Therapeutic Strategy to Combat Cachexia," Medical News Today, 2005.

Li, James and Brainard, Dianna, "Tuberculosis," eMedicine.com, 2004, pp. 1-19.

Walsmith, J. and Roubenoff, R., "Cachexia in Rheumatoid Arthritis," Int. J. Cardiol., 2002, pp. 89-99, vol. 85, No. 1.

Rall, L.C. et al., "Cachexia in Rheumatoid Arthritis is not Explained by Decreased Growth Hormone Secretion," Arthritis Rheum, 2002, pp. 2574-2577, vol. 46, No. 10.

Rall, L.C. and Roubenoff, R., "Rheumatoid Cachexia: Metabolic Abnormalities, Mechanisms and Interventions," Rheumatology, 2004, pp. 1219-1223, vol. 43, No. 10.

Omoto, Atsushi et al., "Copper Chelation with Tetrathiomolybdate Suppresses Adjuvant-Induced Arthritis and Inflammation-Associated Cachexia in Rats," Arthritis Research 7 Therapy, 2005, pp. 1174-1182, vol. 7, No. 6.

Kotler, Donald P., "Cachexia," Annals of Internal Medicine, 2000, 133(8), 622-634.

Oldenburg, H.S. et al., "Cachexia and the acute phase protein response in inflammation are regulated by interleukin-6," Eur. J. Immunol., 1993, 23(8), 1889-1894 (Abstract Only).

Rotter, Victoria et al. "Interleukin-6 (IL-6) induces insulin resistance in 3T3-L1 adipocytes and is, like IL-8 and TNFalpha, overexpressed in human fat cells from insulin-resistant subjects," J. Biol. Chem., Manuscript No. M301977200, Sep. 2, 2003.

Tisdale, Michael J., "Biology of Cachexia," J. Nat'l . Cancer. Inst., 1997, 89(23), 1763-1773.

Shing-Shing Yeh, et a., "Geriatric cachexia: the role of cytokines," Am. J. of Clin. Nutrition, 1999, 70(2), 183-197.

Tisdale, Michael J., "Molecular Pathways Leading to Cancer Cachexia," Physiology, 2005, 20(5), 340-348.

* cited by examiner

*Primary Examiner*—Michael V Meller
*Assistant Examiner*—Qiuwen Mi
(74) *Attorney, Agent, or Firm*—Knoble, Yoshida & Dunleavy LLC (57) ABSTRACT

A method for treatment of cachexia and or alleviating one or more symptoms of cachexia involving the step of administering, to a human or animal, a composition including ingredients obtainable from turmeric, ginger, green tea, and, optionally, horseradish. This composition may further include a pharmaceutically acceptable carrier.

24 Claims, 9 Drawing Sheets

METHOD FOR THE TREATMENT OF CACHEXIA

BACKGROUND OF THE INVENTION

A. Field of the Invention

The present invention relates to a method for the treatment of cachexia. More particularly, the present invention relates to a method for the treatment of cachexia by administration of a composition containing ingredients obtained from turmeric, ginger, and green tea to patients afflicted with an ailment that may cause cachexia.

B. Description of the Prior Art

Cachexia

Cachexia is a potentially fatal wasting of the muscles which appears to be the result of the loss of muscle proteins. Cachexia occurs in several life-threatening diseases, including certain cancers such as lung cancer, pancreatic cancer and cancer of the upper digestive system, AIDS, chronic heart failure, chronic obstructive pulmonary disease, liver failure, emphysema, sepsis, tuberculosis and renal failure. Cachexia also occurs in cases of rheumatoid arthritis. Cachexia is thought to be responsible for about 30% of cancer deaths. This is due to the loss of fat and skeletal muscle that results from cachexia.

Cachexia is thought to be caused by loss of muscle proteins. This loss may be triggered by certain signaling molecules produced by immune-system cells, and by cancer cells. These signaling molecules are cytokines and include, for example, tumor necrosis factor (TNF), typically TNF-alpha, and interferon (IFN)-gamma.

Rheumatoid arthritis is a debilitating, chronic, systemic, autoimmune disease that causes destruction of joint cartilage and bone. It generally occurs between the fourth and sixth decades of life. It is characterized by joint stiffness, pain, and swelling, and is accompanied by a loss of body cell mass. This loss of cell mass, known as rheumatoid cachexia, predominates in skeletal muscle, but also occurs in the viscera and immune system. Thus, rheumatoid cachexia leads to muscle weakness and a loss of functional capacity, and is believed to accelerate morbidity and mortality in rheumatoid arthritis. Rheumatoid cachexia is characterized by elevated resting energy expenditure, accelerated whole-body protein catabolism, and excess production of inflammatory cytokines, tumor necrosis factor alpha and interleukin-1 beta. "Cachexia in Rheumatoid Arthritis," Walsmith, J. and Roubenoff, R., *Int. J Cardiol.*, Vol. 85(1), pp. 89-99, September 2002.

Turmeric (*Curcuma longa*)

Turmeric, or Haldi in Hindi, is used very widely as medicine as well as a common ingredient in Indian cooking. The rhizome of turmeric is used in medicine and food as a fine powder. Anti-inflammatory effects of curcumin isolated from *Curcuma longa* were reported in Srimal and Dhawan, Pharmacology of Diferuloyl Methane, a Non-steroidal Anti-inflammatory Agent, *J. Pharm. Pharmac.*, 25:447-452 (1973). Significant anti-inflammatory activity for curcumin, comparable with phenylbutazone and hydrocortisone, was observed by Arora et al. (*Indian Journal of Medical Research*, 1971, 59, 1289-1291). Curcumin, an alkaloid (diferuloyl methane) isolated from the alcoholic extract of turmeric, has been shown to be a potent anti-inflammatory agent. Further work on anti-inflammatory and anti-arthritic activity has also been carried out by Thatte et al. (*Indian Journal of Pharmacology*, 1986, 18 (1), 19-21). Turmeric has been found to have significant anti-inflammatory activity both in acute and chronic models. The therapeutic dose of turmeric, for optimal activity if used alone, is reported to be in the range of 5 to 10 grams of dry powder daily (Patwardhan, U.S. Pat. No. 5,494,668).

Curcumin not only has anti-inflammatory properties but also has anti-oxidant, anti-tumor and other valuable properties. When used in low concentrations, curcumin can inhibit nitric oxide synthase (NOS) and, therefore, inhibit nitric oxide production. For example, Brouet et al. (*Biochem. Biophys. Res. Commun.*, Jan. 17, 1995; 206 (2); 533-40) have reported that NOS activity in soluble extracts of macrophages activated for 6-24 hours in the presence of curcumin (10 microM) was significantly lower that that of macrophages activated without curcumin. Northern-blot and immunoblotting analyses demonstrated that significantly reduced levels of the mRNA and 130-k Da protein of inducible NOS were expressed in macrophages activated with curcumin, compared to those without curcumin activation. Inhibition of NOS induction was maximal when curcumin was added together with lipopolysaccharide (LPS) and interferon-gamma (IFN-gamma) and decreased progressively as the interval between curcumin and LPS/IFN-gamma was increased to 18 hours.

Ginger (*Zingiber officinale*)

Native to southern Asia, ginger is a 2- to 4-foot perennial that produces grass-like leaves up to a foot long and almost an inch wide. Ginger root consists of the underground stem of the plant, with its bark-like outer covering scraped off. Chinese medical texts from the fourth century B.C. suggest that ginger is effective in treating nausea, diarrhea, stomachaches, cholera, toothaches, bleeding, and rheumatism. Ginger was later used by Chinese herbalists to treat a variety of respiratory conditions, including coughs and the early stages of colds.

Ginger has become widely accepted as a treatment for nausea. Even some conventional medical texts suggest ginger for the treatment of the nausea and vomiting of pregnancy, although others are more cautious.

Ginger also gives some relief from muscular discomfort and pain. It inhibits prostaglandin and leukotriene biosynthesis and histamine release. Thus it acts as an anti-inflammatory as well as an antacid agent. It is a dual inhibitor of the lipoxigenase and cycloxigenase system. Ginger contains 1-4% essential oil (oleoresin). Used alone, fresh Ginger typically requires ingestion in substantially high doses (50 grams daily), which is not only inconvenient but can act as an irritant to the gastric mucosa. In dry form, 7 to 10 grams of dry ginger powder is typically taken daily. Such large doses of ginger are extremely inconvenient for the patient and affect patient compliance on a daily basis. (See Potwardhan, U.S. Pat. No. 5,494,668).

Green Tea (*Camellia sinensis*)

Green tea is the dried leaves and leaf buds of the shrub *Camellia sinensis*. It is mainly produced in China and Japan. Dried tea leaves are composed mainly of phytochemicals known as polyphenols (36%), principally flavonols (including catechins), flavonoids, and flavondiols. The leaves also contain plant alkaloids (about 4%), including caffeine, theobromine and theophylline. Much of the research on green tea has been focused on its potential to prevent cancer. Research suggests that the polyphenols in green tea are responsible for a chemopreventive effect (E. Kaegi, *Canadian Medical Association Journal*, 1998, 158: 1033-35).

Horseradish (*Armoracia rusticana*)

Horseradish, a perennial herb (*Armoracia rusticana*, but sometimes classified in other genera) of the family Cruciferae (mustard family), is native to Central and Southern Europe. It is grown mainly for its roots, which formerly were used medicinally, particularly as an antiscorbutic. Horseradish is also an excellent diuretic, and is good for digestion problems. Herbalists combine horseradish and honey for coughs and asthma treatments. Externally, it is sometimes used to alleviate the pain and stiffness caused by rheumatism.

U.S. Pat. Nos. 5,248,504 and 5,385,734, disclose the use of horseradish to treat nasal and sinus dysfunction. Attempts have also been made to provide oral horseradish remedies for certain ailments. U.S. Pat. No. 98,875, relates to a medical compound including pulverized horseradish for alleviating asthma, coughs and colds. U.S. Pat. No. 74,205, discloses a medical compound containing horseradish for the treatment of consumption.

There remains a need for alternative methods for the treatment of cachexia.

Accordingly, it is an object of certain embodiments of the present invention to provide a method for the treatment of cachexia.

This and other objects of the present invention will be apparent from the summary and detailed description of the invention, which follow.

SUMMARY OF THE INVENTION

In one embodiment, the present invention relates to a method for the treatment of cachexia. The method includes the step of administering a composition containing ingredients obtainable from turmeric, ginger and green tea, to a patient afflicted with an ailment that may cause cachexia.

DETAILED DESCRIPTION OF THE PREFERRED EMBODIMENTS

The present invention relates to a method for the treatment of cachexia. The method includes the step of administering to a patient afflicted with an ailment that may cause cachexia, a composition containing ingredients, which can be obtained from turmeric, ginger, horseradish and/or green tea.

As used herein the term, "flavors" includes both fruit and botanical flavors.

As used herein the term, "sweeteners" includes sugars, for example, glucose, sucrose and fructose. Sugars also include high fructose corn syrup solids, invert sugar, sugar alcohols including sorbitol, and mixtures thereof. Artificial sweeteners are also included within the scope of the term, "sweetener."

As used herein, the term, "pharmaceutically acceptable" means a component that is suitable for use with humans and/or animals without undue adverse side effects (such as toxicity, irritation, and allergic responses), commensurate with a reasonable risk/benefit ratio. Further, as used herein, the term "safe and effective amount" refers to the quantity of a component, which is sufficient to yield a desired therapeutic response without undue adverse side effects (such as toxicity, irritation, or allergic responses), commensurate with a reasonable risk/benefit ratio when used in the manner described herein.

As used herein, the term, "effective amount" means an amount that provides a beneficial result in the treatment of cachexia, alleviates at least one symptom of cachexia or prevents onset of cachexia in patients with an ailment that may cause cachexia.

Amounts given in the present application may be generalized to other forms of the various components obtainable from turmeric, ginger, green tea, etc., based on amounts of one or more components found in each form of the component.

Each of turmeric, ginger and green tea contain active ingredients which may provide some beneficial effect in treating cachexia. Turmeric and ginger may further serve as COX-2 inhibitors to treat certain types of inflammation. However, the taste of each of turmeric, ginger, or horseradish at an effective dosage level may be too overpowering for a patient. It has been found that the combination of materials, obtainable from turmeric, ginger and green tea, provides a substantial beneficial effect, as well as favorable taste characteristics which make the composition palatable.

The first ingredient of the composition employed in the method of the present invention is obtainable from turmeric. The yellow pigment of the rhizome of turmeric is composed of three compounds known as curcuminoids. The three curcuminoids are curcumin (diferuloylmethane), desmethoxycurcumin (hydroxycinnamoyl feruloylmethane), and bis-desmethoxycurcumin (dihydroxydicinnamoyl methane) (see Drug Analysis by *Chromatography and Microscopy*, p. 169, Ann Arbor Science Inc., 1973). The essential oils of turmeric (*curcuma longa*) are primarily composed of the following compounds: d-camphor (1%), cyclo-isoprenemyrcene (85%), and p-tolylmethylcarbinol (5%), (see E. Gunther, *The Essential Oil*, pp. 123-4, Van Nostrand Co., 1955). The first ingredient obtainable from turmeric, may include curcuminoids, such as curcumin (diferuloylmethane), desmethoxycurcumin (hydroxycinnamoyl feruloylmethane), and bis-desmethoxycurcumin (dihydroxydicinnamoyl methane), and mixtures of two or more of these curcuminoids.

Methods for isolating curcuminoids from turmeric are known, (see Janaki and Bose, An Improved Method for the Isolation of Curcumin From Turmeric, J. Indian Chem. Soc.

44:985 (1967)). Alternatively, curcuminoids for use in the present invention can be prepared by synthetic methods.

The first ingredient, obtainable from of turmeric, can be incorporated into the composition for use in the method of the present invention in a variety of different forms. Those different forms may include extracts of turmeric such as turmeric powder extracts, turmeric fluid extracts, one or more curcuminoid compounds, turmeric powder, parts of, or whole plants of turmeric, tinctures thereof, and mixtures thereof. For particular active compounds of turmeric for which a suitable synthetic route is known, the compounds may be prepared synthetically. In one specific embodiment, the first ingredient is a turmeric extract, which may be powdered.

The second ingredient of the composition useful in the method of the present invention may be obtained from ginger (also commonly called ginger root). Ginger inhibits prostanoid synthesis and products of 5-lipoxygenase. The potency of the ginger extract in the acute inflammation test appears to be comparable to that exhibited by acetyl salicylic acid reported in the same study. (Mascolo N. et al *Journal of Ethnopharmocology,* 1989, 27, 129-140).

One of the features of inflammation is increased oxygenation of arachidonic acid, which is metabolized by two enzymic pathways—the cyclooxygenase (CO) and the 5-lipoxygenase (5-LO)-leading to the production of prostaglandins and leukotrienes respectively. It is suggested (Srivastava and Mustafa; *Medical Hypotheses* 1992, 39 342-348) that at least one of the mechanisms by which ginger shows its ameliorative effects could be related to inhibition of prostaglandin and leukotriene biosynthesis, i.e. it works as a dual inhibitor of eicosanoid biosynthesis.

Ginger contains 1-4% essential oil (oleoresin). Many chemical investigations have been carried out on the constituents of the essential oil of ginger. Altogether more than 200 different volatiles have been identified in the essential oil of ginger. The essential oil of ginger contains a mixture of various terpenes as well as some other non-terpenoid compounds.

The active compounds of ginger which may be employed in the present invention include, but are not limited to, 1,8-cineole, 10-dehydrogingerdione, 10-gingerol, 6-gingerdione, 6-gingerol, 6-shogaol, 8-β-17-epoxy-λ-trans-12-ene-15,16-diol, 8-gingerol, 8-shogaol, 9-oxo-nerolidol, acetaldehyde, acetic acid, alanine, α-linolenic-acid, α-linolenic acid, α-phellandrene, α-piene, α-terpinene, α-terpineol, α-zingiberene, ar-curcumene, arginine, ascorbic acid, asparagine, β-bisabolol, β-carotene, β-elemene, β-eudesmol, β-ionone, β-myrcene, β-phellandrene, β-pinene, β-selinene, β-sesquiphellandrene, β-sitosterol, β-thujone, bornyl-acetate, boron, caffeic acid, calcium, camphene, camphor, capric acid, caprylic acid, capsaicin, caryophyllene, chavicol, chlorogenic acid, chromium, citral, citronellal, citronellal, cobalt, copper, cumene, curcumin, cystine, delphinidin, δ-cadinene, elemol, ethyl acetate, ethyl-myristate, farnesal, farnesene, ferulic acid, furfural, γ-aminobutyric acid, γ-terpinene, geranial, geraniol, geranyl-acetate, gingerenone, glutamic acid, glycine, hexahydrocurcumin, histidine, isogingerenone-B, isoleucine, kaempferol, lecithin, limonene, linoleic acid, magnesium, manganese, methionine, mufa, myrecene, myricetin, myristic acid, neral, nerol, nerolidol, niacin, nickel, oleic acid, oxalic acid, p-coumaric acid, p-cymene, p-hydroxy-benzoic acid, palmitic acid, pantothenic acid, paradol, patchoulic alcohol, phenylalanine, quercetin, riboflavin, selenium, shikimic-acid, terpinen-4-ol, thiamin, tryptophan, vanillic acid, vanillin, zinc, and zingerone. Also, mixtures of two or more of these active compounds may be employed.

The second ingredient of the composition useful in the method of the present invention, obtainable from ginger, can be incorporated in many different forms including extracts such as ginger powder extracts, ginger fluid extracts, ginger powder including ginger root powder, one or more active compounds of ginger, parts of, or whole ginger plants, tinctures thereof, and mixtures thereof. Also, for any specific active compound of ginger for which suitable synthesis routes are known, the active compound can be prepared synthetically. In certain embodiments, the second ingredient of the composition is selected from ginger root extract, ginger root powder and powdered ginger root extract.

The composition useful in the method of the present invention may further include a third ingredient, obtainable from green tea. The third ingredient obtainable from green tea may have an antioxidant effect. The pharmacological activities of green tea are mainly due to its active compounds. The active compounds of green tea useful in the present invention include, but are not limited to, flavonols, catechins, flavonoids, flavondiols, plant alkaloids, caffeine, theobromine, theophylline, phenolic acids, proteins, carbohydrates, and minerals.

The third ingredient of the composition useful in the method of the present invention, obtainable from green tea, can be included in the form of green tea powder, green tea extracts such as green tea powder extracts and green tea fluid extracts, one or more active compounds of green tea, part of, or whole green tea plants, green tea leaves, tinctures thereof, or mixtures thereof. The green tea powder can be produced by grinding green tea leaves. The green tea extract may be produced by extracting from dry green tea leaves using common extraction methods. For a particular active compound of green tea, for which a synthetic route is known, the active compound may be synthesized. Alternatively, the green tea powder, the green tea extract and/or the active compounds of green tea can be purchased from commercial sources such as Delavau Co.

The third ingredient of the composition obtainable from green tea, may be selected from green tea leaves, green tea powder and green tea extract. Alternatively, the third ingredient of the composition is powdered green tea extract.

A fourth, optional ingredient of the composition useful in the method of the present invention is obtainable from horseradish, also commonly called horseradish root. Horseradish's pharmacological activities are mainly due to its active compounds. The active compounds of horseradish which may be useful in the present invention include, but are not limited to, allyl-isothiocyanate, amylase, arginine, ascorbic acid, asparagine, gentisic acid, kaempferol, limonene, niacin, p-hydroxy-benzoic acid, pectin, phenylpropyl-isothiocyanate, quercetin, raphanin, riboflavin, rutoside, selenium, sinapic acid, sinigrin, tannin, thiamin, vanillic acid and zinc, as well as mixtures of two or more of these compounds.

The fourth, optional ingredient of the composition useful in the method of the present invention, obtainable from horseradish, can be included in many different forms. Those different forms include horseradish powder, horseradish extracts such as horseradish powder extracts and horseradish fluid extracts; one or more active compounds of horseradish, parts of, or whole plants of horseradish, tinctures thereof, and mixtures thereof. For a particular active compound, for which a synthetic route is known, the active compound may be prepared synthetically. In certain embodiments, the fourth, optional ingredient of the composition obtainable from horseradish may be selected from horseradish powder, horseradish root extract and horseradish root oil.

All active compounds of the present invention may be obtained from other sources, if available. Thus, the phrase "which can be obtained from" or the phrase "which may be obtained from" is meant to encompass compounds or compositions that are obtainable from turmeric, ginger, horseradish or green tea and therefore encompasses synthetic forms of the same compounds and/or compositions as well as the same compounds and/or compositions obtained from other sources.

The ingredients of the composition useful in the method of the present invention may be extracted using common extraction procedures. One suitable extraction procedure is described below. The extraction procedure comprises, generally, the steps of:
1) cleaning the plant from which the pharmacologically or biologically active plant extract is to be obtained to remove any foreign matter thereon;
2) particulating the plant to obtain a particulate mass having particle size ranging from 0.001 to about 10 $mm^3$; and
3) subjecting the particulate mass to at least one polar and at least one non-polar solvent to obtain separate fractions of plant extract soluble in the respective solvents, and mixing the fractions so obtained to obtain the beneficiated plant extract in accordance with this invention.

For instance, in the case of turmeric, the process comprises the steps of:
1) cleaning the roots of turmeric to remove any foreign matter thereon;
2) particulating the roots to obtain a particulate mass having particle size ranging from 0.001 to about 10 $mm^3$;
3) subjecting the particulate mass to distillation to obtain a volatile fraction, if any, from the particulate mass;
4) cooking the distilled particulate mass in a polar solvent, such as water to solubulize material in the distillation-treated particulate mass to obtain first solution and a first residue;
5) filtering the first solution from the first residue;
6) evaporating the filtrate obtained from the first solution to remove the solvent and obtain a solute designated as fraction A obtained from the particulate mass;
7) subjecting the first residue to treatment with a second polar solvent such as 75% to 95% ethanol for twelve to thirty-six hours to obtain a second solution and a second residue;
8) filtering the second solution from the second residue to obtain a second filtrate;
9) evaporating the second filtrate to remove its solvent and obtain a solute designated as fraction B obtained from the particulate mass;
10) subjecting the second residue to less polar or non-polar solvents, such as petroleum ether, for twelve to thirty-six hours to obtain a third solution and a third residue, and filtering the third solution from the third residue to obtain a third filtrate;
11) evaporating the third filtrate to remove its solvent and obtain a solute designated as fraction C obtained from the particulate mass; and
12) homogeneously mixing the volatile fraction, with fractions A, B and C from the particulate mass to obtain a beneficiated plant extract.

The foregoing extraction procedure is suitable for the preparation of pharmacologically or biologically active plant extracts in a convenient, administrable dosage form from any of the plants mentioned above.

Solvents useful for extracting turmeric include water, ethanol, propanol, paraffin, hexane, petroleum ether, toluene, acetone, methyl ethyl ketone, and other common organic solvents. Water, ethanol and petroleum ether are particularly useful solvents for extracting turmeric. Solvents useful for extracting ginger include water, ethanol, propanol, paraffin, petroleum ether, hexane, toluene, acetone, methyl ethyl ketone, and other common organic solvents. Ethanol, water and acetone are the best solvents for extracting ginger. Solvents useful for extracting horseradish include water, ethanol, propanol, paraffin, petroleum ether, hexane, toluene, acetone, methyl ethyl ketone, and other common organic solvents. Water and ethanol are the best solvents for extracting horseradish.

One composition for use in the method of the present invention includes powdered turmeric extract, powdered ginger root extract, powdered green tea extract, and, optionally, horseradish root oil, each in a safe and effective amount to provide one or more of the beneficial effects described herein.

The composition useful in the method of the present invention may further include a suitable demulcent, which may soothe and mobilize mucous membrane in the mouth of a patient. The demulcent may be obtained from slippery elm. Alternatively, the demulcent may be selected from pectin, mucilage and carageenan. The active compounds of slippery elm, which may be useful in the present invention as a demulcent, include, but are not limited to, ascorbic acid, $\beta$-carotene, $\beta$-sitosterol, citrostadienol, magnesium, manganese, mucilage, niacin, riboflavin, selenium, tannin, thiamin, zinc and mixtures thereof.

The demulcent, when obtained from slippery elm, may be incorporated into the composition of the present invention in a form selected from slippery elm bark powder, slippery elm extracts such as slippery elm powder extracts, slippery elm fluid extracts, one or more active compounds of slippery elm, slippery elm bark, tinctures thereof, and mixtures thereof. Slippery elm bark powder may be produced by grinding slippery elm bark. Slippery elm extract may be produced by extracting from slippery elm bark using well-known extraction processes. For a particular active compound, for which a synthetic route is known, the active compound may be synthesized.

Alternatively, the slippery elm bark powder, the slippery elm extract and/or the active compounds of slippery elm may be purchased from commercial sources such as Delavau Co. The demulcent may be selected from slippery elm extract and slippery elm bark powder. Each gram of the composition for use in the method of the present invention may contain 50 mg to 150 mg of slippery elm bark powder as the demulcent. Alternatively, each gram of the composition of the invention may contain 75 mg to 120 mg of slippery elm bark powder as the demulcent.

In another embodiment, the composition of the present invention may further include other natural COX-2 inhibitors such as ingredients obtainable from one or more of Chinese goldthread and barberry, holy basil, baikal skullcap, Hu zhang (Japanese Knotweed), rosemary, oregano, feverfew and hops. The additional ingredients, which may exhibit COX-2 inhibiting properties include, but are not limited to, one or more of apigenin, baicalein, berberine, catechins, eicosapentaenoic-acid, eugenol, evodiame, evodol, humulone, kaemperol, oleanolic acid, parthenolide, resveratrol, rutaecarpine, salicylic acid, trans-reveratrol and ursolic acid. These additional ingredients can be incorporated in the composition of the present invention in the form of a powder, a part of, or a whole plant, a powder extract, a fluid extract, a tincture, when applicable, and mixtures thereof. Alternatively, if a suitable synthetic route is known, these additional, optional ingredients may be prepared by synthetic methods.

The composition of the present invention may be formulated using a safe and effective amount of the three main ingredients obtainable from tumeric, ginger and green tea, to provide one or more of the beneficial effects of the invention described herein, and one or more of the optional ingredients mentioned above, including, but not limited to ingredients obtainable from horseradish and slippery elm, COX-2 inhibitors, as well as one or more of the additional optional ingredients described below. The composition of the present invention may also be formulated with a pharmaceutically acceptable carrier.

The composition of the present invention may be formulated in any orally acceptable dosage form including, but not limited to, capsules, tablets, lozenges, troches, hard candies, powders, sprays, gels, elixirs, syrups, and suspensions or solutions.

The pharmaceutically acceptable carrier may include, but is not limited to: (a) carbohydrates including sweeteners, such as, fructose, sucrose, sugar, dextrose, starch, lactose, maltose, maltodextrins, corn syrup solids, honey solids, commercial tablet compositions including EMDEX®, MOR-REX®, ROYAL-T®, DI-PAC®, SUGAR-TAB®, SWEET-REX®, and NEW-TAB®; (b) sugar alcohols including mannitol, sorbitol and xylitol; and (c) various relatively insoluble excipients including dicalcium phosphate, calcium sulfate, calcium carbonate, microcrystalline cellulose and other pharmaceutical tableting ingredients.

Lozenges, tablets, and troches in this invention may differ in shape, size and manufacturing technique. In the case of tablets, for oral use, the pharmaceutically acceptable carrier may further include lactose and corn starch. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin, PEG-8000 and gum acacia.

In the case of lozenges for oral use, the common pharmaceutically acceptable carrier may further include a binder such as PEG-8000. Lozenges may weigh 0.1 to 15 grams to provide a suitable dissolution rate when taken orally. Alternatively, lozenges may weigh 1 to 6 grams.

To make compressible lozenges, the active ingredients are added to PEG-8000 processed fructose; or the active ingredients of the composition are added to crystalline fructose and commercially available, sweet, direct compression products such as Mendell's SUGARTAB®, SWEETREX®, or EMDEX®. Additional optional ingredients may include sweeteners, such as saccharin, if desired, and flavors, as desired, glidants, such as silica gel, as needed, and lubricants, such as magnesium stearate, as needed. The mixture should be kept dry and tableted soon after mixing. The ingredients are mixed and directly compressed into lozenges using conventional pharmaceutical mixing and tableting equipment. The compressive force may be sufficient to produce maximum hardness throughout the lozenges, to preserve a suitable dissolution rate, and to maximize the efficacy of the lozenges. The composition may be stored in an airtight container and in a cool dark place.

Tablets and troches can be manufactured using procedures similar to that described above with minor changes in the optional ingredients. Such changes are within the skill of the ordinary skilled artisan.

Alternatively, the composition of the present invention may be formulated in liquid form, such as syrups, mouthwashes or sprays, with a solvent or dispersant such as water, or other liquids and optionally in a pharmaceutically acceptable carrier, for repeated delivery of the composition to oral and oropharyngeal mucous membranes over a sustained period of time. Alternatively, such formulations can be in a concentrated form suitable for dilution with water or other materials prior to use.

The composition may also be formulated in chewable forms, such as soft candy, gum drops, liquid filled candies, and chewing gum bases, or in the form of dental products, such as toothpastes and mouthwashes. Dental products may be used in the ordinary manner of using such products.

The composition of the invention may be formulated in capsule form, with or without diluents. For capsules, useful diluents include lactose and dried corn starch. When suspensions are employed, emulsifying and/or suspending agents may be employed in the suspensions. In addition, solid compositions including one or more of the ingredients of the lozenges described above may be employed in soft and hard gelatin capsules.

The composition of the present invention may also be formulated into a nasal aerosol or inhalant composition. Such a composition may be prepared using well-known techniques. For these types of formulations, suitable carriers may include the following ingredients: saline with one or more preservatives, absorption promoters to enhance bioavailability, fluorocarbons, and/or conventional solubilizing or dispersion agents.

Other materials, which may optionally be included in the composition of the present invention, include inositol, other B-complex vitamins, and anti-inflammatories. Also, ingredients such as sweeteners, flavorants, coloring agents, dyes, preservatives, emulsifying agents, suspending agents, melting agents, excipients, and solvents or diluents such as water, ethanol, propylene glycol, glycerin and various combinations thereof, may be included in the composition of the present invention.

The optional sweeteners which may be used in the composition of the present invention include, but are not limited to, saccharin, aspartame, cyclamates, acesulfame K, neohesperidin dihydrochalcone, other super sweeteners, and mixtures thereof, which may be added to the carrier in amounts sufficiently low so as not to chemically interact with the main ingredients of the composition.

The optional flavorants which may be used in the composition of the present invention include, but are not limited to, peppermint, peppermint-menthol, eucalyptol, wintergreen, licorice, clove, cinnamon, spearmint, cherry, lemon, orange, lime, menthol and various combinations thereof.

The three main ingredients described above which may be derived from turmeric, ginger and green tea, may make up from about 0.5-90% by weight of the total composition of the composition. Alternatively, the three main ingredients may make up 10-70% by weight of the total composition. In another embodiment, the three main ingredients make up 20-40% by weight of the total composition.

The non-carrier ingredients of the composition, including, for example, the ingredients obtainable from turmeric, ginger, green tea, and, optionally, horseradish and slippery elm, as discussed above, can be increased or decreased proportionally in the composition of the present invention depending on the amount of carrier used in the composition, without substantially affecting the effectiveness of the composition for its intended use.

The present invention also relates to a method of treating cachexia by administering a therapeutically effective amount of the composition of the present invention to a patient with an ailment that may cause cachexia. Cachexia occurs in several life-threatening diseases, including certain cancers such as lung cancer, pancreatic cancer and cancer of the upper digestive system, AIDS, chronic heart failure, chronic obstructive pulmonary disease, liver failure such as chronic liver failure, emphysema, sepsis, tuberculosis and renal failure.

Also, the present invention relates to a method of treating cachexia by administering a therapeutically effective amount of the composition of the present invention to a patient suffering from cachexia.

The effective amount of the composition will vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the composition, and the severity of the illness or symptom. It is within the skill of the person of ordinary skill in the art to account for these factors.

An effective amount of the composition for each administration may contain, for example, a total of 0.01 gram to 1 gram of the three main ingredients, obtainable from turmeric, ginger, and green tea. An effective amount of the composition for each administration may contain a total of 0.2 gram to 0.5 gram of the three main ingredients obtainable from turmeric, ginger and green tea.

The method of the present invention involves the administration of a composition of the present invention to a patient that suffers from cachexia or to a patient afflicted with an ailment that may cause cachexia. The composition may be administered 1-15 times per day, as needed, alternatively, 2-12 times per day, as needed, or 6-10 times per day, as needed. As discussed above, the composition of the present invention may be administered to a patient in any orally acceptable dosage form including, but not limited, to tablets, capsules, lozenges, troches, hard candies, powders, oral sprays, nasal sprays, gels, elixirs, syrups, chewable compositions, dental products, suspensions and solutions.

Each of the various methods of the present invention may be applied with humans or animals.

A daily dose of the composition useful in the present invention may contain a sufficient amount of a composition obtainable from turmeric to provide from about 0.03 mg to about 1500 mg of curcumin, a component of turmeric. Alternatively, a daily dose of the composition may contain a sufficient amount of a composition obtainable from turmeric to provide from about 0.6 mg to about 750 mg of curcumin. In another embodiment, the daily dose of the composition may contain a sufficient amount of a composition obtainable from turmeric to provide from about 1 mg to about 100 mg of curcumin.

A daily dose of the composition of the present invention may contain a sufficient amount of a composition obtainable from ginger to provide from about 0.05 mg to about 100 mg of gingerols, a component of ginger root extract. Alternatively, a daily dose of the composition may contain a sufficient amount of a composition obtainable from ginger to provide from about 0.5 mg to about 25 mg of gingerols. In another embodiment, the daily dose of the composition may contain a sufficient amount of a composition obtainable from ginger to provide from about 1 mg to about 10 mg of gingerols.

A daily dose of the composition useful in the method of the present invention may contain a sufficient amount of a composition obtainable from green tea to provide from about 0.09 mg to about 7200 mg of catechins, a component of green tea extract. Alternatively, a daily dose of the composition may contain a sufficient amount of a composition obtainable from green tea to provide from about 2 mg to about 3600 mg of catechins. In another embodiment, the daily dose of the composition may contain a sufficient amount of a composition obtainable from green tea to provide from about 10 mg to about 2000 mg of catechins.

A daily dose of the composition of the present invention may optionally contain a sufficient amount of horseradish root oil to provide from about 0.0036 mg to about 0.36 mg of allyl isothiocyanate, a component of horseradish root oil. Alternatively, a daily dose of the composition of the present invention may optionally contain a sufficient amount of horseradish root oil to provide from about 0.005 mg to about 0.2 mg of allyl isothiocyanate. In another embodiment, a daily dose of the composition of the present invention may optionally contain a sufficient amount of horseradish root oil to provide from about 0.01 to about 0.1 mg of allyl isothiocyanate.

Amounts given in the present application may be applied to other types of compositions obtainable from turmeric, ginger, green tea and horseradish, based on the content of these other types of compositions of the stated components, curcumin, gingerols, catechins and allyl isothiocyanate. Thus, the concentration of curcumin, gingerols, catechins and allyl isothiocyanate in a particular composition obtainable from turmeric, ginger, green tea and horseradish may vary so long as an amount of the extract is employed which provides the above-mentioned daily dosages of curcumin, gingerols, catechins, and allyl isothiocyanates, respectively. Also, as discussed above, the daily dose may be administered as a single dose or several smaller doses, as desired.

The invention will be further illustrated by the examples given below which are not to be construed as limiting the invention in any way. The scope of the invention is to be determined by the claims appended hereto.

EXAMPLES

Example 1

A Composition of the Present Invention

A composition of the present invention was prepared by mixing the following ingredients:

| Active Ingredients | |
|---|---|
| Powdered Extract of Ginger Root (5% gingerols) | 28.00 mg |
| Horseradish Root Oil | 0.35 mg |
| Powdered Turmeric extract (30% curcuminoids) | 2.60 mg |
| Powdered Extract of Green Tea (85% catechins) | 13.50 mg |
| Inactive Ingredients | |
| Cellulose | 147.05 mg |
| Calcium Silicate | 3.50 mg |
| Magnesium Stearate | 3.00 mg |
| Silicon dioxide (silica) | 2.00 mg |

Example 2

Cytotoxicity and Cytokine Inhibition

The composition of Example 1 was tested for cytotoxicity and cytokine inhibition using the following procedures.

Ten male DO11.10 mice (TcR specific for Ovalbumin) five weeks old were employed as TcR Tg lymph node cell donors. The cells were harvested by removing peripheral (PLN) and mesenteric (MLN) cells from the DO11.10 ovalbumin specific TcR Tg mice. Lymph node single cell suspensions were made by passing through nitex mesh. Cell suspensions were aliquoted into well plates at $2\times10^6$ lymphocytes per ml, using 1 ml per well. The cells were cultured at 5% $CO_2$ and 37° C.

Two separate well plates were set up for each of the 24 hour and 48 hour time points employed in the test. 200 mg of the composition of Example 1 were diluted with 52 microliters of glycerine and 948 microliters of RPMI 1640 tissue culture media containing 10% fetal calf serum, 2 mM of L-glutamine, 100 IU/ml penicillin and 100 µg/ml streptomycin to provide an initial solution of 200 mg/ml of the composition of Example 1. Further dilutions were then made to this solution to provide solutions having eight different concentrations of the composition of Example 1 using suitable amounts of RPMI 1640 tissue culture media.

Tests were conducted for eight different concentrations of the composition of Example 1, namely, concentrations of active ingredients of 1 mg/ml (Concentration 1), 0.1 mg/ml (Concentration 2), 0.01 mg/ml (Concentration 3), 0.001 mg/ml (Concentration 4), 0.0001 mg/ml (Concentration 5), 0.00001 mg/ml (Concentration 6), 0.000001 mg/ml (Concentration 7) and 0.0000001 mg/ml (Concentration 8). Each of the eight different concentrations were tested on the mouse cells in vitro, both in the presence of Ovalbumin and in the absence of Ovalbumin by addition to wells containing 500 microliters of cells with and without Ovalbumin. Chicken egg Ovalbumin, catalog number A5503 from Sigma was employed at a concentration of 1 mg/ml in sterile phosphate buffered saline (PBS), supplied by Sigma in pre-sterilized form.

At day 0, half of the TcR Tg lymph node cells were stimulated by contact with 1 mg/ml of albumin in sterile PBS, with the remainder being treated by the same amount of sterile PBS alone. Some of the wells were then treated with the composition of Example 1 at different concentrations. The composition was added to the appropriate wells and remained for the duration of the study.

At 24 and 48 hours, the number of live/dead cells per ml was counted by Trypan blue for each treatment group. The supernatant from each treatment group was harvested and frozen at −20° C. Multiplex cytokine analysis by Luminex was carried out for interleukin-2, interleukin-4, interleukin-10, interleukin-12, IFN-γ and TNF-α. The results are shown in FIGS. 1-8. In FIGS. 5-8, the bar represents the mean value and the line extending upward and downward from each bar in the graph represents the standard error of the mean value represented by each bar in the graph.

Examples 3-7

In Vivo Testing for Cachexia

A formulation was made using the ingredients shown in Table 1:

TABLE 1

| Ingredients | Amount (grams) | Weight Percent |
|---|---|---|
| Glycerin | 5 | 4.94 |
| PE Turmeric 30% | 0.246 | 0.24 |
| PE Ginger 5% | 2.65 | 2.62 |
| Horseradish Oil | 0.033 | 0.03 |
| PE Green Tea 90% | 1.28 | 1.26 |
| TOTAL | 9.209 | 9.10 |
| Standard PBS | 92 | 90.90 |
| TOTAL | 101.209 | 100 |

NOTES:

PE = Powdered Extract

PBS = Phosphate Buffer Solution

The PBS was added to the 9.2 of extract to come up with the stock solution 0.5 ml was injected to deliver 5 mg of ingredients other than PBS per injection.

Examples 3-6

The effect of a 0.5 ml injection of the composition of Table 1 on the induction and progression of cachexia was tested in a well characterized tumor model. In this model, BALB/C mice are injected s.c. with $0.5\times10^6$ MC-26 murine colon carcinoma cells (day 0) and different groups of mice are also injected with 0.5 ml of the composition of Table 1 at different time points as indicated in Table 2 and FIG. 9. The mice are weighed every 2-3 days starting at day 7 and every day starting at day 14. The cell dose was determined in a separate set of experiments in which different cell doses were injected into groups of five animals. $0.5\times10^6$ MC-26 were found to be the optimal number of cells for this experiment.

Figure 1:
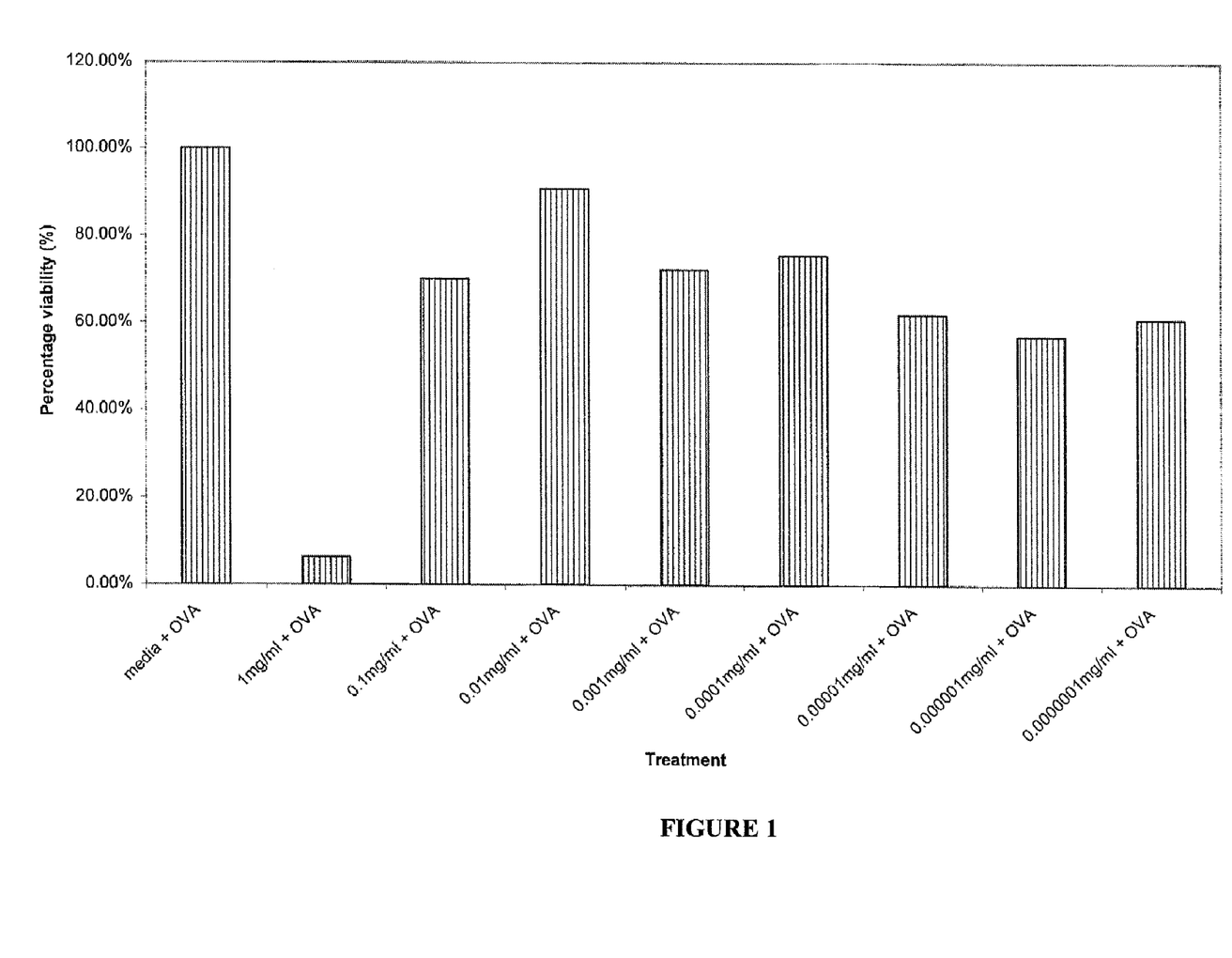
FIG. 1 is a graph of the cell viability at 24 hours following stimulation with Ovalbumin (OVA) and incubation with various concentrations of the composition of Example 1.
Figure 2:
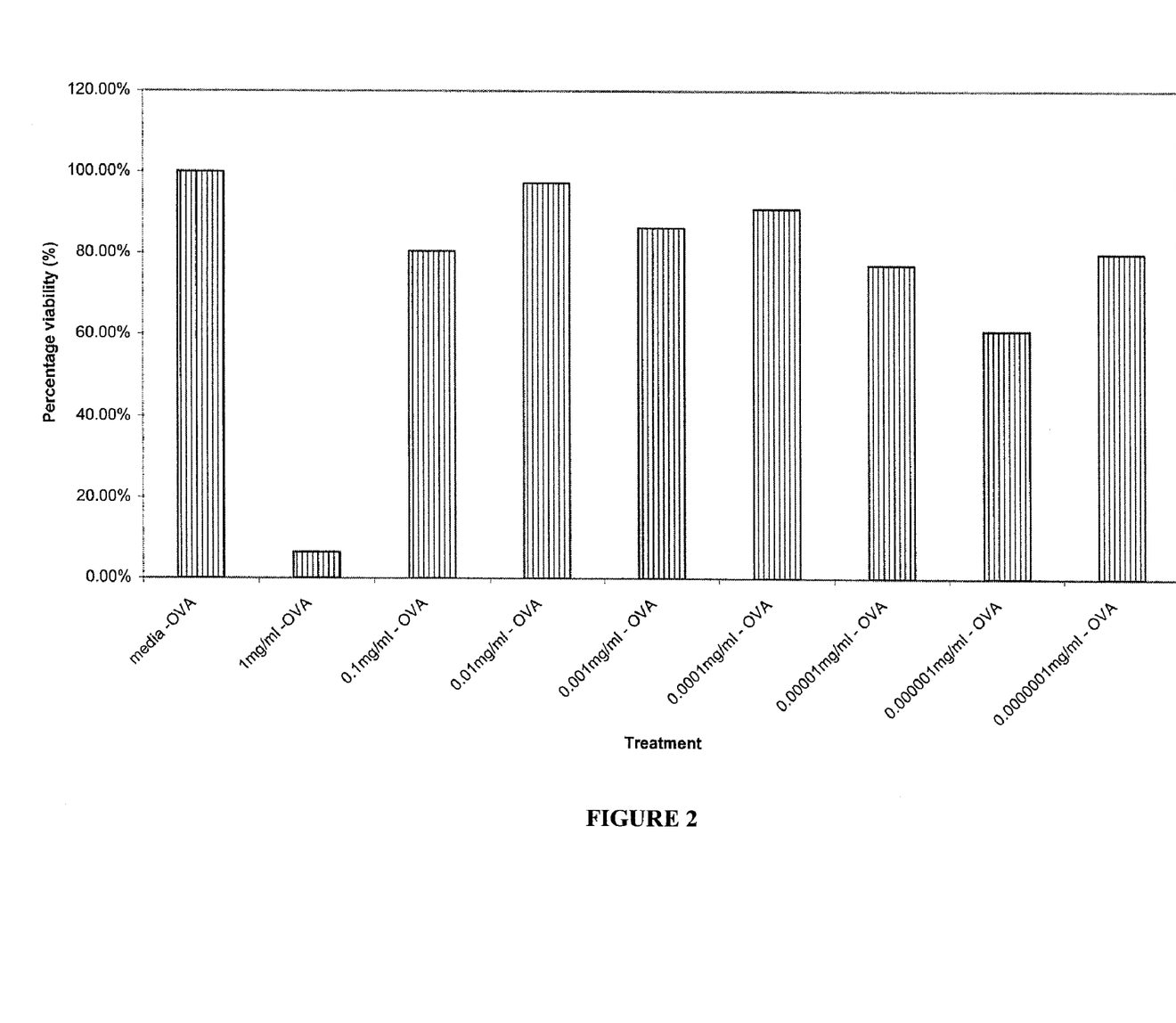
FIG. 2 is a graph of the cell viability at 24 hours following incubation with various concentrations of the composition of Example 1.
Figure 3:
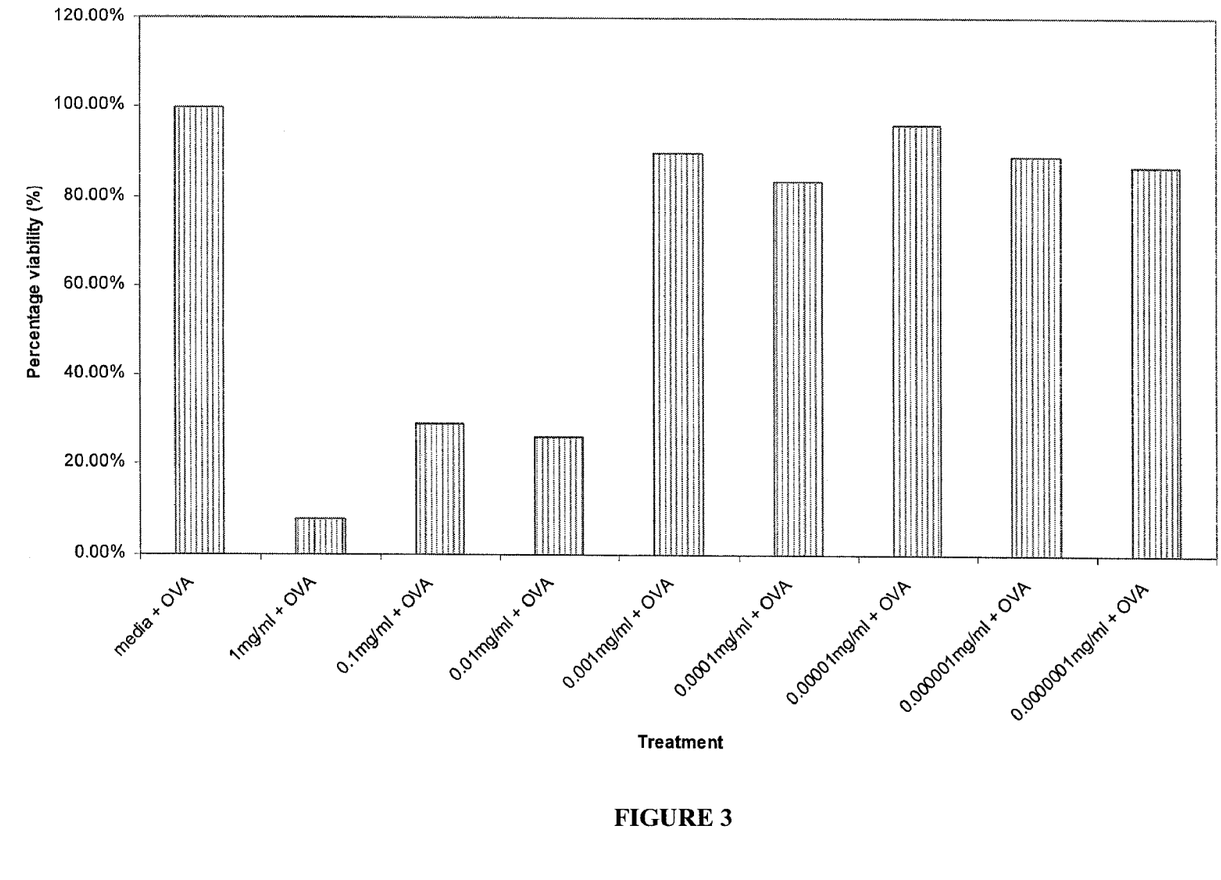
FIG. 3 is a graph of the cell viability at 48 hours following stimulation with Ovalbumin (OVA) and incubation with various concentrations of the composition of Example 1.
Figure 4:
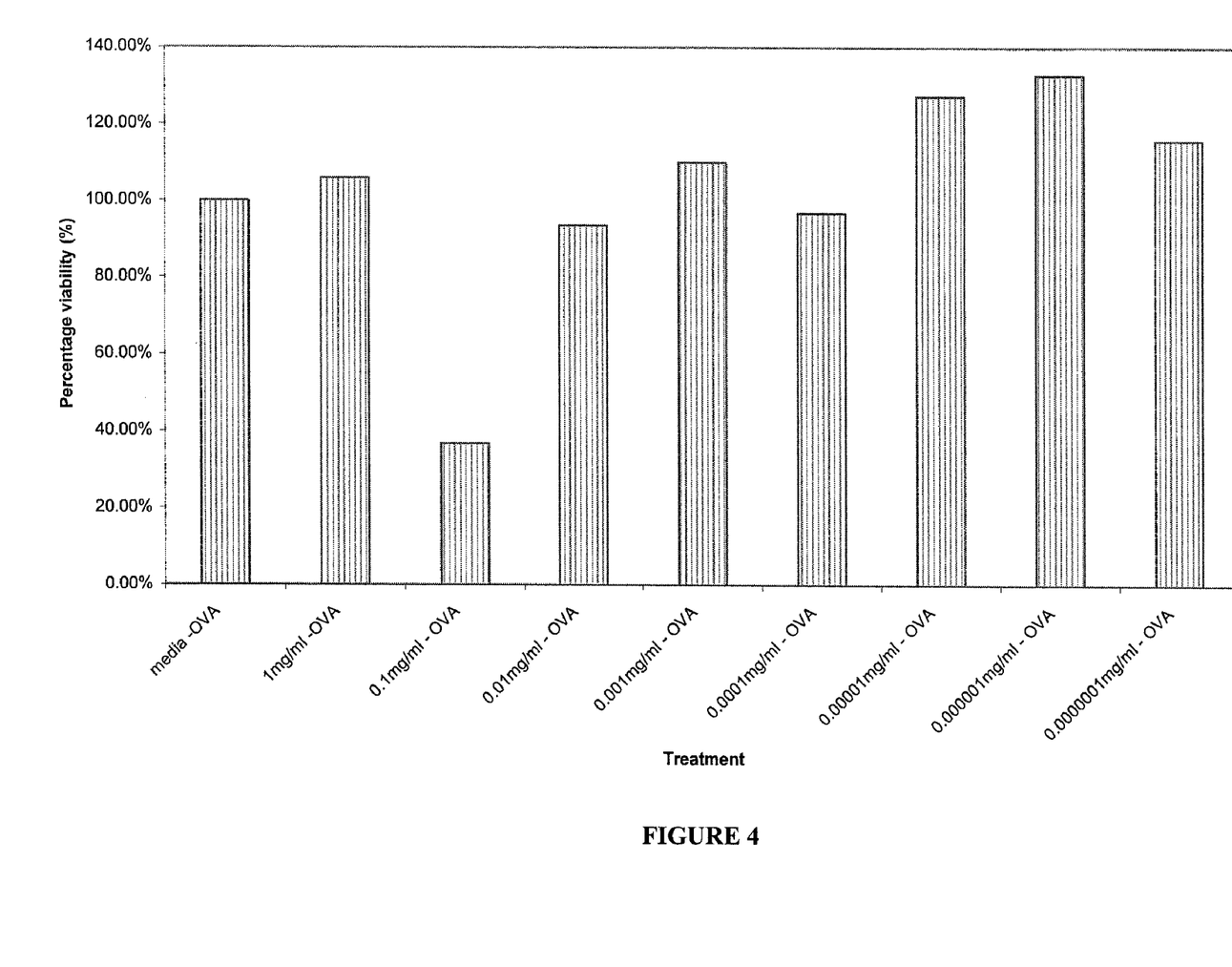
FIG. 4 is a graph of the cell viability at 48 hours following incubation with various concentrations of the composition of Example 1.
Figure 5:
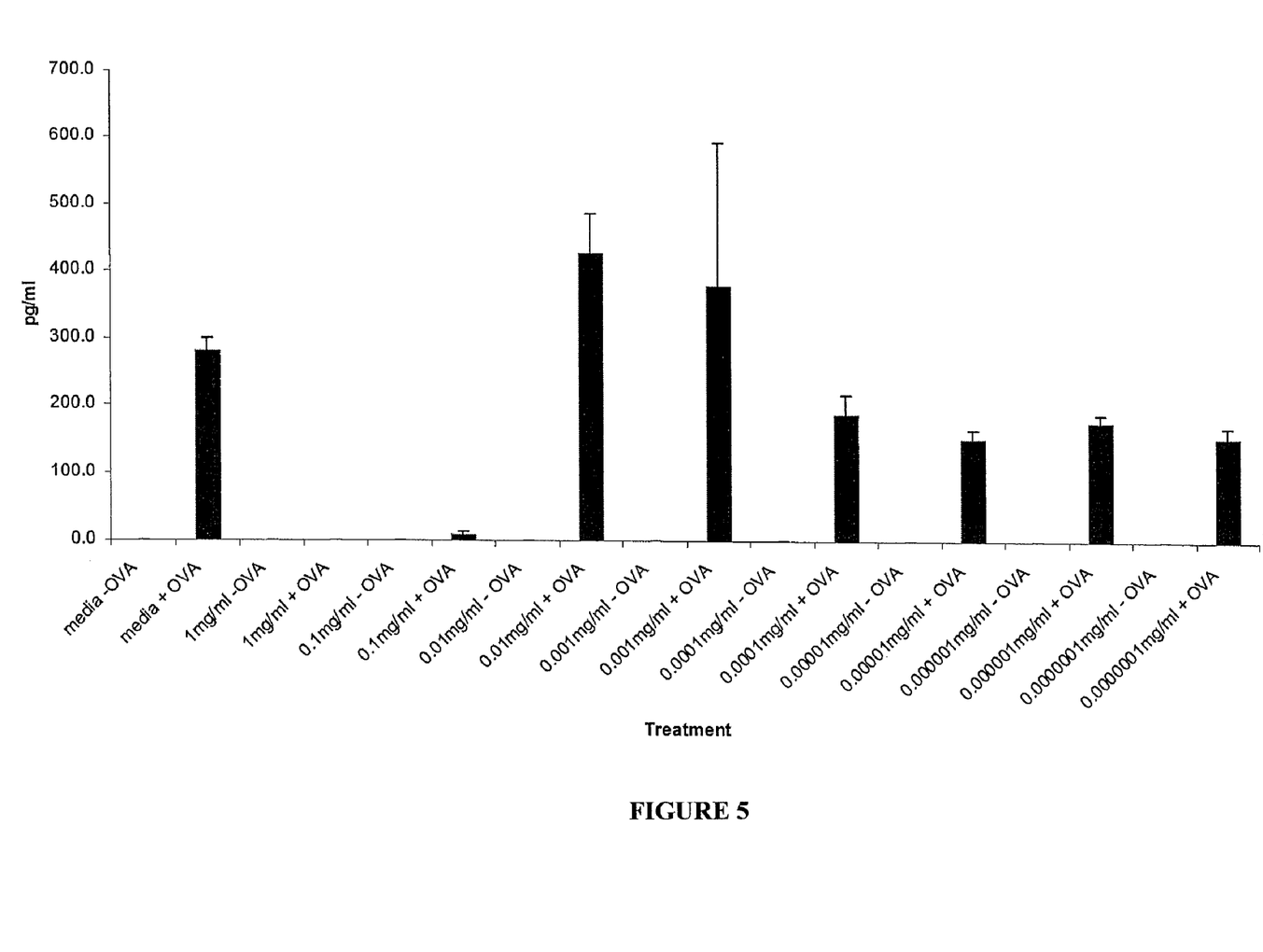
FIG. 5 is a graph of interferon-γ levels at 24 hours following incubation with various concentrations of the composition of Example 1, with and without OVA stimulation.
Figure 6:
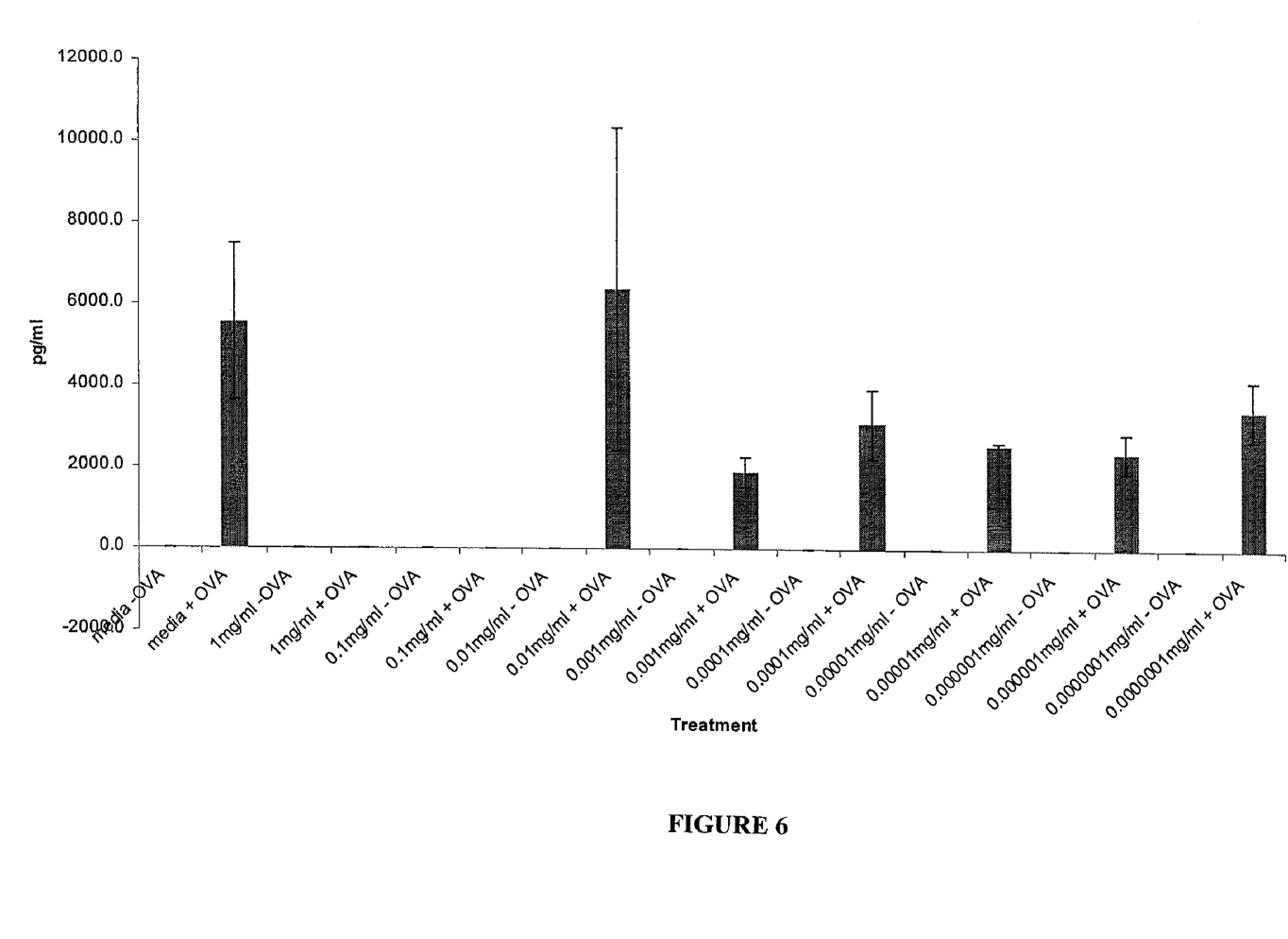
FIG. 6 is a graph of interferon-γ levels at 48 hours following incubation with various concentrations of the composition of Example 1, with and without OVA stimulation.
Figure 7:
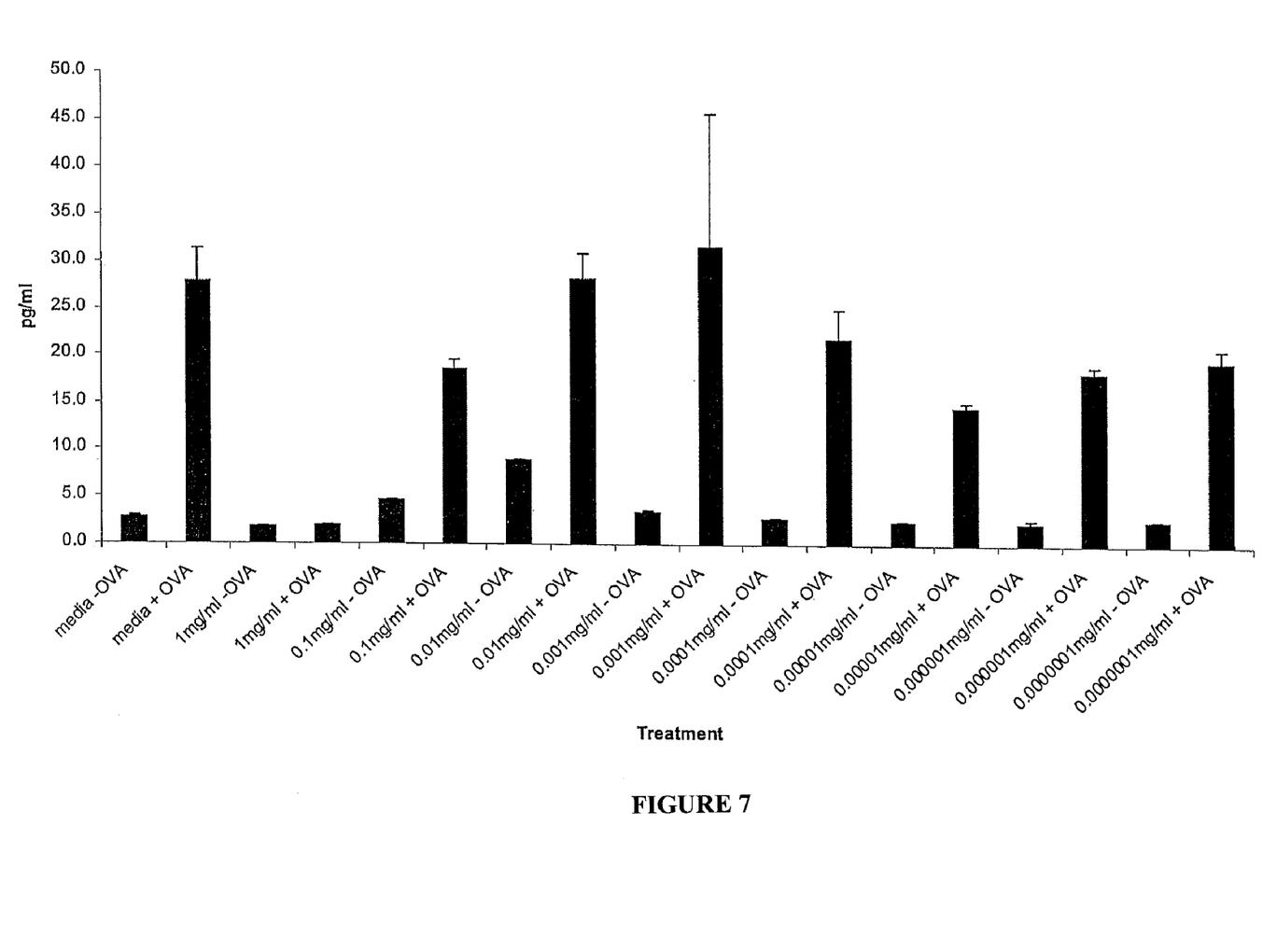
FIG. 7 is a graph of tumor necrosis factor-α levels at 24 hours following incubation with various concentrations of the composition of Example 1, with and without OVA stimulation.
Figure 8:
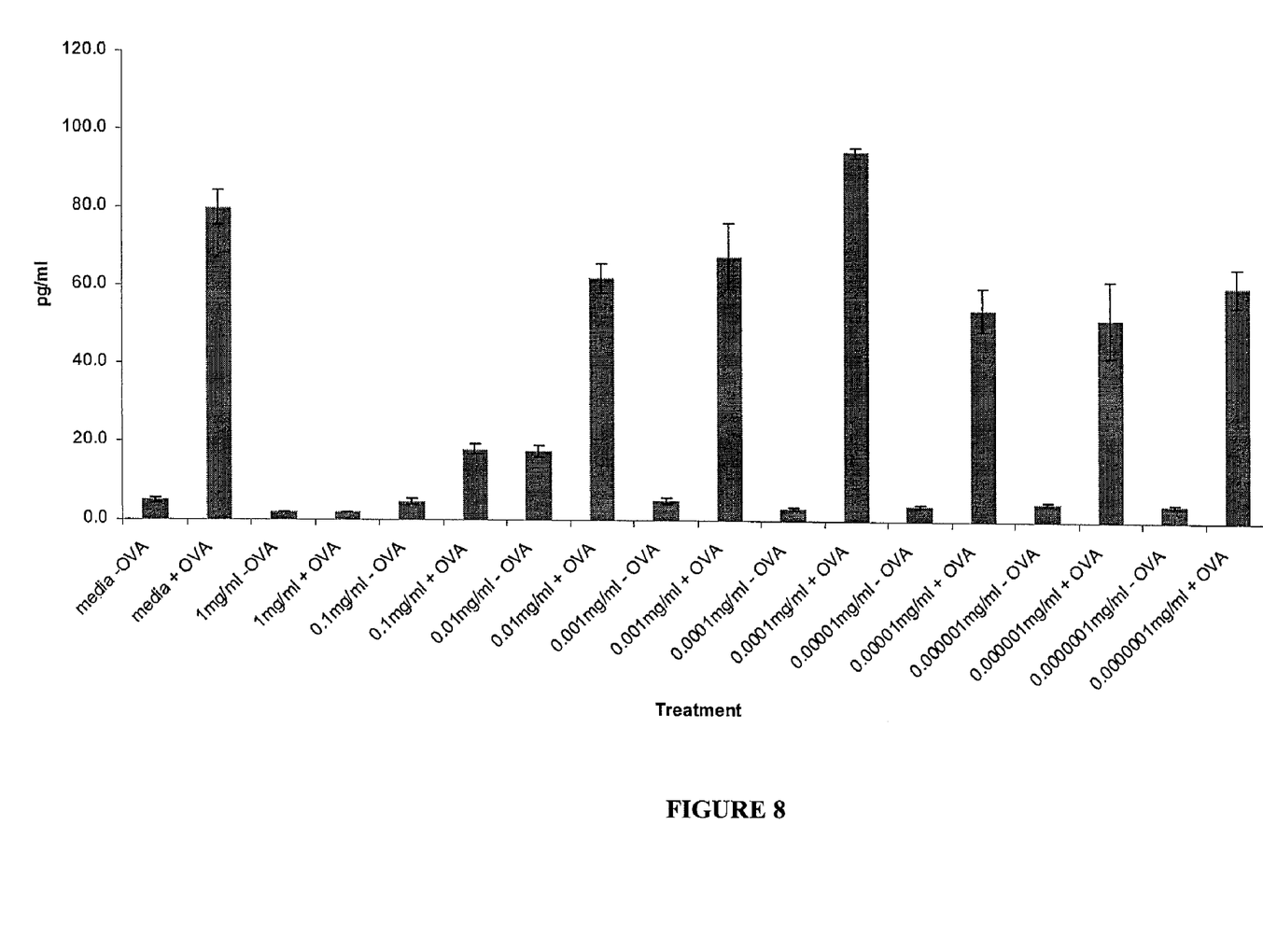
FIG. 8 is a graph of tumor necrosis factor-α levels at 48 hours following incubation with various concentrations of the composition of Example 1, with and without OVA stimulation.
Figure 9:
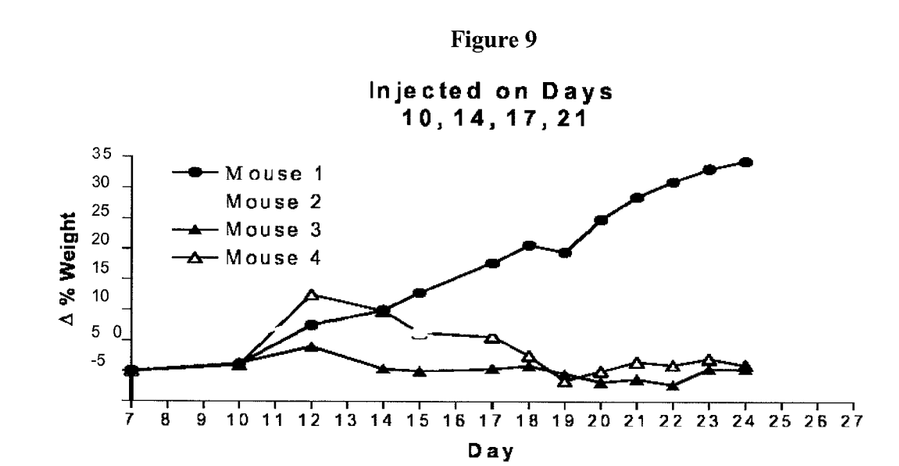
FIG. 9 is a graph of the percentage weight change in mice injected s.c. with $0.5 \times 10^6$ MC-26 murine colon carcinoma cells over time for Examples 3-6.

The results are presented in Table 2 and FIG. 9. The data indicate that mice injected with 5 mg of the composition of Table 1 on days 10, 14, 17 and 21 were clearly protected from cachexia. Three out of the four mice in this group did not exhibit significant weight loss whereas all three untreated control animals exhibited 15-25 percent weight loss at the end of the experiment (day 24). In this example, one out of the four mice in the responsive groups did not respond at all. Both groups had similar size tumors averaging 1.25 cm in diameter.

TABLE 2

| Injected at (Days) | | Day 7 g | Day 10 g | Δ% | Day 12 g | Δ% | Day 14 G | Δ% | Day 15 g | Δ% | Day 17 g | Δ% | Day 18 g | Δ% |
|---|---|---|---|---|---|---|---|---|---|---|---|---|---|---|
| 10 | 1 | 24.1 | 23.8 | 1.2 | 22.3 | 7.5 | 21.7 | 10.0 | 21 | 12.9 | 19.8 | 17.8 | 19.1 | 20.7 |
| 14 | 2 | 25.1 | 23.9 | 4.8 | 22.9 | 8.8 | 23.4 | 6.8 | 23.5 | 6.4 | 23.3 | 7.2 | 23.2 | 7.6 |
| 17 | 3 | 22.7 | 22.4 | 1.3 | 21.8 | 4.0 | 22.6 | 0.4 | 22.7 | 0.0 | 22.6 | 0.4 | 22.5 | 0.9 |
| 21 | 4 | 19.2 | 19 | 1.0 | 16.8 | 12.5 | 17.3 | 9.9 | 18 | 6.3 | 18.1 | 5.7 | 18.7 | 2.6 |
| Control | 1 | 24.8 | 24.3 | 2.0 | 24.1 | 2.8 | 24.2 | 2.4 | 24.4 | 1.6 | 25 | −0.8 | 24.8 | 0.0 |
| | 2 | 25.8 | 25.2 | 2.3 | 25.5 | 1.2 | 25.3 | 1.9 | 25.7 | 0.4 | 25.5 | 1.2 | 25.6 | 0.8 |
| | 3 | 20.8 | 19.8 | 4.8 | 19.9 | 4.3 | 19.3 | 7.2 | 20 | 3.8 | 19.9 | 4.3 | 19.7 | 5.3 |

TABLE 2-continued

| | Injected at (Days) | Day 19 g | Day 19 Δ% | Day 20 g | Day 20 Δ% | Day 21 g | Day 21 Δ% | Day 22 g | Day 22 Δ% | Day 23 g | Day 23 Δ% | Day 24 g | Day 24 Δ% |
|---|---|---|---|---|---|---|---|---|---|---|---|---|---|
| Normal | | 19.1 | 19 | 0.5 | 19.1 | 0.0 | 18.6 | 2.6 | 19.1 | 0.0 | 19.4 | −1.6 | 18.9 | 1.0 |
| | 10 | 1 | 19.4 | 19.5 | 18.1 | 24.9 | 17.2 | 28.6 | 16.6 | 31.1 | 16.1 | 33.2 | 15.8 | 34.4 |
| | 14 | 2 | 23.5 | 6.4 | 23.7 | 5.6 | 23.4 | 6.8 | 23.4 | 6.8 | 23.5 | 6.4 | 23.1 | 8.0 |
| | 17 | 3 | 22.8 | −0.4 | 23.1 | −1.8 | 23 | −1.3 | 23.2 | −2.2 | 22.6 | 0.4 | 22.6 | 0.4 |
| | 21 | 4 | 19.5 | −1.6 | 19.2 | 0.0 | 18.9 | 1.6 | 19 | 1.0 | 18.8 | 2.1 | 19 | 1.0 |
| | Control | 1 | 24.6 | 0.8 | 24.3 | 2.0 | 23.7 | 4.4 | 24.1 | 2.8 | 22.4 | 9.7 | 21.4 | 13.7 |
| | | 2 | 25.3 | 1.9 | 24.2 | 6.2 | 22.7 | 12.0 | 22 | 14.7 | 19.8 | 23.3 | 19.5 | 24.4 |
| | | 3 | 19.7 | 5.3 | 19.3 | 7.2 | 18 | 13.5 | 16.5 | 20.7 | 16.1 | 22.6 | 15.7 | 24.5 |
| Normal | | 19.1 | 0.0 | 19 | 0.5 | 18.7 | 2.1 | 19.7 | −3.1 | 19.2 | −0.5 | 19.3 | −1.0 |

Note: first Normal row header is at top; first row of numeric entries appears offset by one column in the original layout.

Example 7

In this example, injections were started at day 10 and later. The composition of Table 1 was injected into four groups of mice, five animals per group, at the time points indicated in FIG. 10. The rest of the conditions (number of tumor cells and amount of composition administered) were the same as in Examples 3-6.

Figure 10:
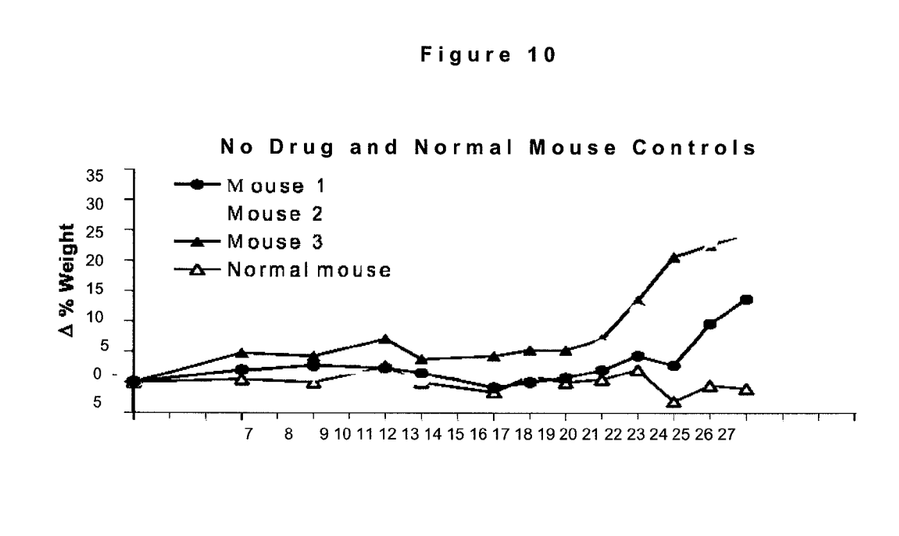
FIG. 10 is a graph of the percentage weight change in mice injected s.c. with $0.5 \times 10^6$ MC-26 murine colon carcinoma cells over time for Example 7.

The results confirmed that the best protection from weight loss was achieved in the group that was injected every 3-4 days starting at day 10 ending at day 21. In this example, one out of the four mice in the responsive groups did not respond at all. The kinetics of weight changes show that within the responsive mice, some mice initially showed significant weight loss but then regained some of the weight back. Protection from weight loss diminished when mice were injected starting at day 14 and no substantial effect was observed when injections started on day 17.

Changes may be made in carrying out the methods and to the compositions of the invention above set forth above without departing from the spirit and scope of the invention. It is intended that all matter contained in the above description shall be interpreted as illustrative and not in a limiting sense. The scope of this invention is to be determined from the claims appended hereto.

I claim:

1. A method for the treatment of cachexia comprising the step of administering, to a human or animal afflicted with an ailment selected from the group consisting of cancer, AIDS, chronic heart failure, chronic obstructive pulmonary disease, liver failure, emphysema, sepsis, tuberculosis and renal failure and in need of such treatment, an effective amount of a composition comprising a first ingredient selected from the group consisting of turmeric powder extracts, turmeric fluid extracts, one or more curcuminoid compounds, turmeric powder, parts of or whole plants of turmeric, tinctures thereof, and mixtures thereof; a second ingredient selected from the group consisting of ginger powder extracts, ginger fluid extracts, ginger powder, ginger root powder, parts of or whole ginger plants, tinctures thereof, and mixtures thereof; a third ingredient selected from the group consisting of green tea powder, green tea powder extracts, green tea fluid extracts, parts of or whole green tea plants, green tea leaves, tinctures thereof, or mixtures thereof; and a fourth ingredient selected from the group consisting of horseradish powder, horseradish powder extracts, horseradish fluid extracts, parts of or whole plants of horseradish, tinctures thereof, and mixtures thereof.

2. A method as claimed in claim 1, wherein the step of administering the composition is carried out 1 to 15 times per day.

3. A method as claimed in claim 1, wherein the step of administering the composition is carried out 2 to 12 times per day.

4. A method as claimed in claim 1, wherein the step of administering the composition is carried out 1 to 6 times per day.

5. A method as claimed in claim 1, wherein a daily dose of the composition comprises from about 0.03 mg to about 1500 mg of curcumin.

6. A method as claimed in claim 1, wherein a daily dose of the composition comprises from about 0.6 to about 750 mg of curcumin.

7. A method as claimed in claim 1, wherein a daily dose of the composition comprises from about 1 to about 100 mg of curcumin.

8. A method as claimed in claim 5, wherein the daily dose of the composition comprises from about 0.05 mg to about 100 mg of gingerols.

9. A method as claimed in claim 6, wherein the daily dose of the composition comprises from about 0.5 mg to about 25 mg of gingerols.

10. A method as claimed in claim 7, wherein the daily dose of the composition comprises from about 1 mg to about 10 mg of gingerols.

11. A method as claimed in claim 8, wherein the daily dose of the composition comprises from about 0.09 mg to about 7200 mg of catechins.

12. A method as claimed in claim 9, wherein the daily dose of the composition comprises from about 2 mg to about 3600 mg of catechins.

13. A method as claimed in claim 10, wherein the daily dose of the composition comprises from about 10 mg to about 2000 mg of catechins.

14. A method as claimed in claim 1, wherein a daily dose of the composition comprises from about 0.0036 mg to about 0.36 mg of allyl isothiocyanates.

15. A method as claimed in claim 1, wherein a daily dose of the composition comprises from about 0.005 mg to about 0.2 mg of allyl isothiocyanates.

16. A method as claimed in claim 1, wherein the daily dose of the composition comprises from about 0.01 mg to about 0.1 mg of allyl isothiocyanates.

17. A method as claimed in claim 1, wherein the patient is afflicted with cancer.

18. A method as claimed in claim 17, wherein the patient is afflicted with a cancer selected from the group consisting of: lung cancer, pancreatic cancer and cancer of the upper digestive system.

19. A method as claimed in claim 1, wherein the patient is afflicted with chronic heart failure.

20. A method as claimed in claim 1, wherein the patient is afflicted with sepsis.

21. A method as claimed in claim 1, wherein the patient is afflicted with tuberculosis.

22. A method as claimed in claim 1, wherein the patient is afflicted with renal failure.

23. A method as claimed in claim 1, wherein the patient is afflicted with liver failure.

24. A method as claimed in claim 1 wherein the patient is afflicted with emphysema.

* * * * *